(12) United States Patent
Friedl

(10) Patent No.: US 6,224,601 B1
(45) Date of Patent: May 1, 2001

(54) OSTEOSYNTHESIS AUXILIARY FOR THE TREATMENT OF SUBTROCHANTERIC, PERITOCHANTERIC AND FEMORAL-NECK FRACTURES

(75) Inventor: Wilhelm Friedl, Aschaffenburg (DE)

(73) Assignee: Endocare AG, Rotkreuz (CH)

( * ) Notice: Subject to any disclaimer, the term of this patent is extended or adjusted under 35 U.S.C. 154(b) by 0 days.

(21) Appl. No.: 09/552,451

(22) Filed: Apr. 18, 2000

Related U.S. Application Data

(62) Division of application No. 09/271,065, filed on Mar. 17, 1999, which is a division of application No. 08/966,077, filed on Nov. 7, 1997, now Pat. No. 5,928,235, which is a division of application No. 08/564,045, filed on Apr. 4, 1996, now Pat. No. 5,713,902.

(30) Foreign Application Priority Data

Jun. 1, 1993 (DE) .................................................. 43 18 150

(51) Int. Cl.$^7$ ...................................................... A61B 17/78
(52) U.S. Cl. ............................................................ 606/64
(58) Field of Search ............................. 606/62, 64, 65, 606/66, 67, 68, 63

(56) References Cited

U.S. PATENT DOCUMENTS

| | | |
|---|---|---|
| 3,433,220 | 3/1969 | Zickel . |
| 3,561,437 | 2/1971 | Orlich . |
| 4,103,683 | 8/1978 | Neufeld . |
| 4,697,585 | 10/1987 | Williams . |
| 4,895,572 | 1/1990 | Chernoff . |
| 4,978,349 | 12/1990 | Frigg . |

FOREIGN PATENT DOCUMENTS

| | | |
|---|---|---|
| 8701164 | 7/1987 | (DE) . |
| 3730570 | 3/1989 | (DE) . |
| 9102018 | 6/1991 | (DE) . |
| 9207026 | 11/1992 | (DE) . |
| 257118 | 3/1988 | (EP) . |
| 321170 | 6/1989 | (EP) . |
| 486483 | 5/1992 | (EP) . |
| 491138 | 6/1992 | (EP) . |
| 521600 | 1/1993 | (EP) . |
| 586824 | 3/1994 | (EP) . |
| 2688360 | 4/1992 | (FR) . |
| 2209947 | 6/1989 | (GB) . |

Primary Examiner—Michael Buiz
Assistant Examiner—David O. Reip
(74) Attorney, Agent, or Firm—Knobbe, Martens, Olson & Bear, LLP

(57) ABSTRACT

Osteosynthesis auxiliary (10) for the treatment of subtrochanteric, peritrochanteric and femoral-neck Fractures, with a locking nail (12) that can be introduced from the proximal end into the medullary space of a femur (11) and that comprises a distal section (15) having at least one oblong cross bore (13) to receive a distal locking element as well as a proximal section (14) having a slanted passageway (16), and with a femoral-neck part (19) that can be introduced from a lateral position through the slanted passageway (16) into the neck (17) and head (18) of the femur, wherein at least the section of the femoral-head part that can be anchored in the head (18) of the femur has a cross section that is not circular or rotationally symmetrical. Preferably this section (34) has the shape of a double-T or I profile (35). At the end away from the head (18) of the femur the femoral-neck blade (19) also comprises a radially projecting collar (33) to limit the lateral extent to which the femoral-neck blade (19) can be inserted into the passageway (16) through the locking nail (12).

4 Claims, 3 Drawing Sheets

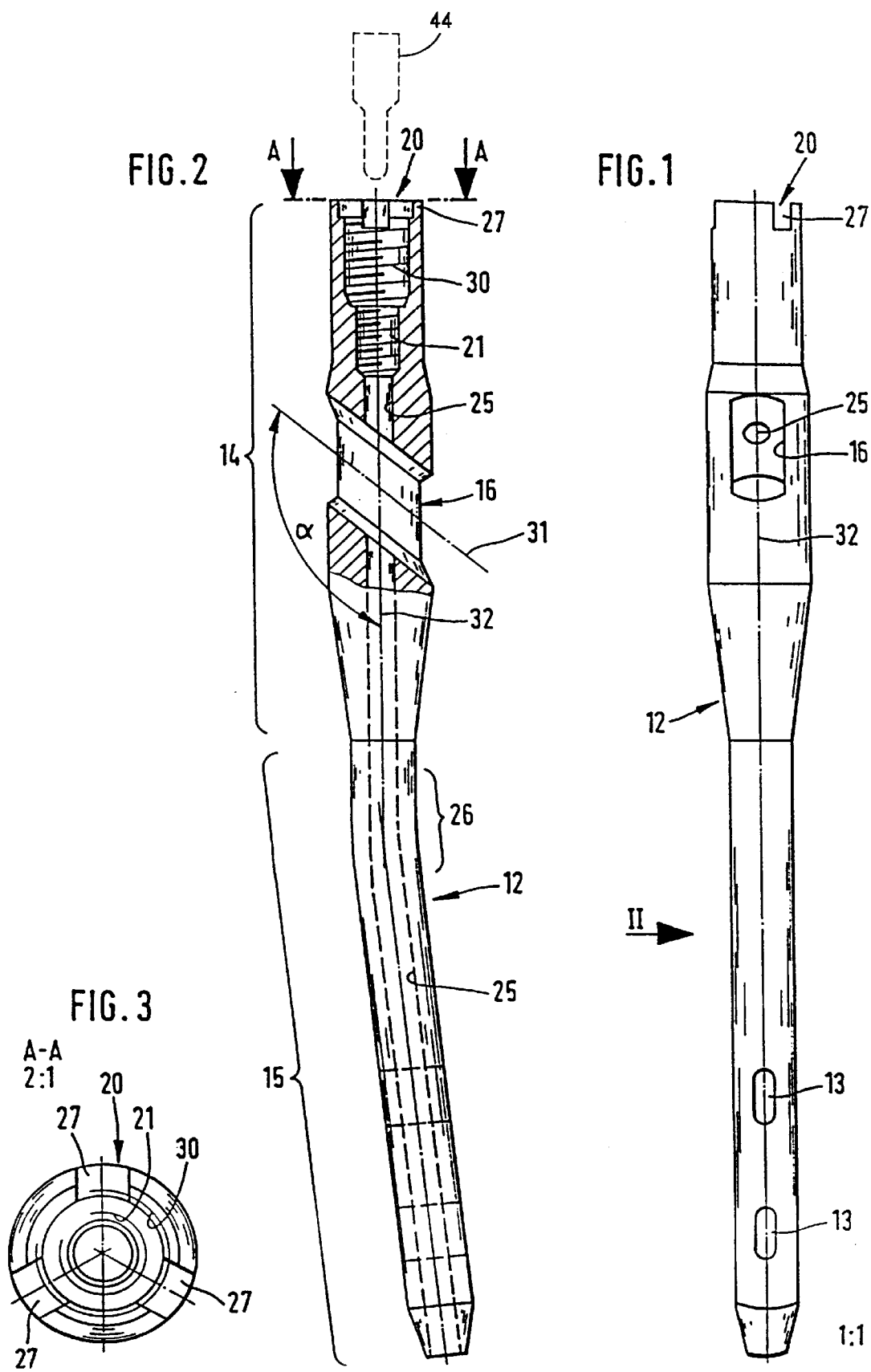

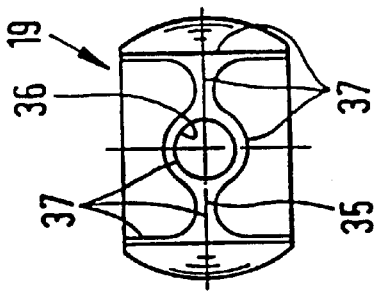
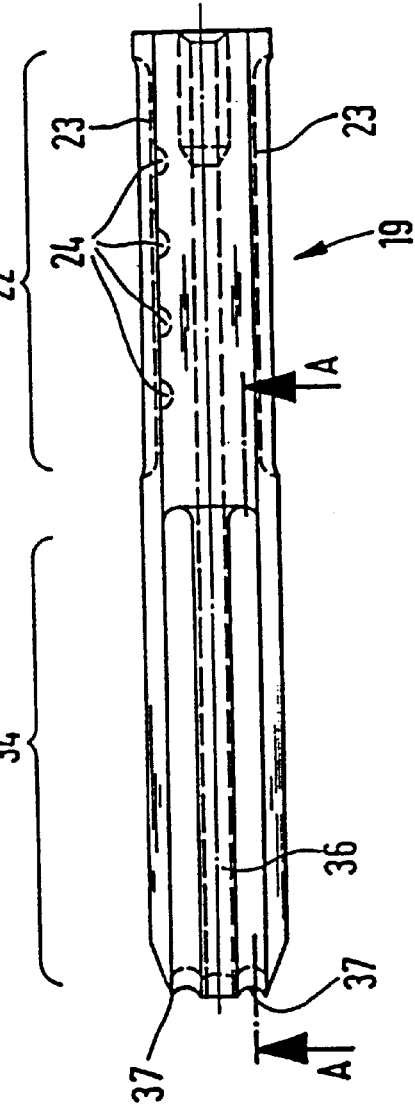
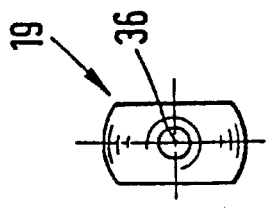
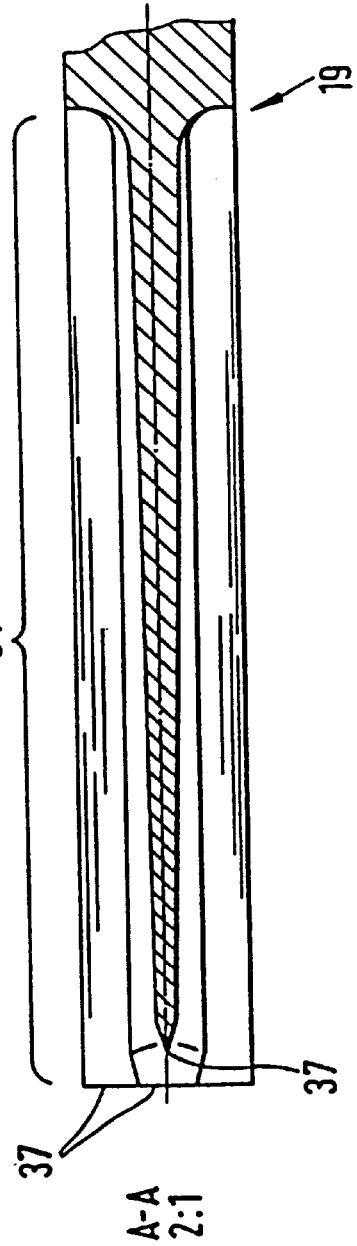

OSTEOSYNTHESIS AUXILIARY FOR THE TREATMENT OF SUBTROCHANTERIC, PERITOCHANTERIC AND FEMORAL-NECK FRACTURES

This application is a divisional application of U.S. patent application Ser. No. 09/271,065, filed Mar. 17, 1999, which in turn, is a divisional application of U.S. patent application Ser. No. 08/966,077, filed Nov. 7, 1997, now U.S. Pat. No. 5,928,235 which is, in turn, a divisional application of U.S. patent application Ser. No. 08/564,045, filed Apr. 4, 1996, now U.S. Pat. No. 5,713,902.

DESCRIPTION

The invention relates to an osteosynthesis auxiliary for the treatment of subtrochanteric and peritrochanteric fractures as well as fractures of the neck of the femur, with a locking nail that can be introduced from the proximal end into the medullary space of a femur, which comprises a distal region having at least one transverse bore to receive a distal locking element and a proximal section through which passes a slanted passageway, and with a femoral-neck part that can be introduced from a lateral position through the slanted passageway into the neck and head of the femur, such that there can be inserted into the proximal end of the locking nail a stay-pin or the like by means of which the axial movement of the femoral-neck part within the slanted passageway in the proximal section of the locking nail can be either limited or completely blocked.

An osteosynthesis auxiliary of this kind has been disclosed, e.g. in EP 0 257 118 B1. Supplementary information can be found in EP 0 486 483 A1, EP 0 521 600 A1, EP 0 321 170 A1 or DE-U 87 01 164.6. In the known osteosynthesis auxiliaries the locking nail serves to guide and hold a femoral-neck screw. For this purpose the locking nail comprises in its proximal region a slanted bore traversing the nail, through which the femoral-neck screw can be passed. At the end of the femoral-neck screw toward the head of the femur a self-cutting thread is provided, with which anchoring in the head of the femur is achieved. In addition, into the proximal end of the locking nail a stay-pin can be inserted, by means of which the femoral-neck screw is secured against rotation. This stay-pin simultaneously cooperates with axial grooves at the circumference of the femoral-neck screw to limit the axial movement of the femoral-neck screw within the slanted bore of the locking nail. Alternatively, the stay-pin can be used to produce a rigid connection between femoral-neck screw and locking nail.

One disadvantageous feature of the known construction is that in case of a peritrochanteric fracture it is possible for the head of the femur to twist with respect to the femoral-neck screw. Here it should be kept in mind that a not inconsiderable part of the femoral-neck screw lies within the relatively soft spongiosa of the neck of the femur. Only the self-cutting thread extends into the relatively firm spongiosa of the head of the femur. Under severe stress, this thread is not Guaranteed to be rotationally stable with respect to the head-neck fragment, so that the above-mentioned twisting of the head of the femur can result.

Accordingly, it is the object of the present invention to develop an osteosynthesis auxiliary of the known kind in such a way that twisting of the head of the femur is reliably avoided in cases of peritrochanteric fractures or fractures of the neck of the femur, while retaining the known principle of sliding between locking nail and femoral-neck part. This object is achieved by the invention. By constructing the femoral-neck part as a femoral-neck blade in accordance with the invention, said blade is firstly held within the locking nail in a rotationally stable manner, and secondly it secures the head of the femur against twisting.

Because of the special construction and arrangement of the femoral-neck blade according to the invention, such that the flat sides of the femoral-neck blade extend parallel to the long axis of the locking nail or the neck of the femur, the femoral-neck blade is additionally endowed with a particularly high resistance to bending in the plane defined by the femoral-neck blade and locking nail. Accordingly, the femoral-neck blade in accordance with the present invention can sustain extremely large bending moments with no danger that the blade will be deformed in such a way as to prevent its axial movement within the slanted passageway through the locking nail with consequent loss of the above-mentioned sliding principle. In the known constructions with femoral-neck screw this phenomenon of a secondary rigid connection between femoral-neck screw and locking nail has been known to occur, with the consequence that in femoral-neck fractures and fractures in the trochanteric region (extending downward from lateral to medial: Types A1 and A2 in the AO classification of peritrochanteric fractures), the desired compression of the fractured head of the femur or head-neck fragment in the plane of fracture into the metaphyseal fragment becomes impossible and the implant perforates into the hip joint.

In a manner known per se, the locking nail is preferably made hollow throughout, so that it can be introduced into the proximal femur by way of a guide spike. The wall thickness of the hollow locking nail is about 1.5 to 2.5, in particular about 2.0 mm.

In the plane defined by the locking nail and femoral-neck blade the proximal section of the locking nail is bent laterally outward by an angle of 4° to 8°, in particular about 6°, with respect to the distal section, achieve a minimal tension-line concentration in the locking slide nail. In the known construction, the above-mentioned angle is about 12°. This distinct bend in the locking nail causes instabilities when alternating loads are imposed in the region of the bend, and the compromise in accordance with the invention avoids these. Care should also be taken that the transition between distal and proximal sections is not abrupt but constitutes a curved section. In principle, of course it would be advantageous for the locking nail to be exactly straight, because this construction would give it the greatest resistance to buckling. However, such a solution is not useful for reasons of surgical technique; that is, the bending is necessary so that the site of nail insertion can be in the region of the trochanteric tip and not in the region of the fossa. The latter would involve a considerable interference with the blood flow through the head-neck fragment, where circulation is already impeded by the fracture. Furthermore, insertion of a locking nail in the region of the trochanteric fossa is very complicated technically, so that the construction in accordance with the invention is an ideal compromise between technically simple insertion on the one hand and reduction of the tension-line concentration in the locking nail on the other.

The length of the locking nail is between 150 and 350 mm, in particular about 220 mm for the treatment of peritrochanteric fractures and about 320 mm for the treatment of subtrochanteric and pathological fractures. The somewhat shorter locking nail is straight as seen along a line parallel to the plane defined by the locking nail and femoral-neck blade. Hence the locking nail can have the same shape for both the right and the left femur. The somewhat longer design must allow for the curvature of the femur by having a ventral convexity with a radius of about 1.5 m. In this case there must be one locking nail for the right femur and a separate locking nail for the left femur.

In all cases the distal end of the locking nail is preferably rounded, so that it can be gently introduced into the medullary space of the femur.

A measure of special significance for the stability of the system in accordance with the invention is that the width of the proximal section of the locking nail in the region of the slanted passageway for the femoral-neck blade and in the direction perpendicular to this passageway is greater than the width or outside diameter of the region of the locking nail distal to this section. The transitions between the regions of different width in each case should be not abrupt but rather slightly curved, to avoid tension peaks. This construction reliably avoids breakage of the locking nail in the region of the passageway for the femoral-neck blade. This region is extremely critical with regard to stability, as it represents a weak point which furthermore is relatively heavily loaded by way of the femoral-neck blade. By means of the above-mentioned measures a sufficient resistance to breakage is achieved in the critical region around the slanted passageway for the femoral-neck blade.

At the proximal end of the locking nail there are uniformly spaced around its circumference at least two, preferably three recesses to enable form-fitting engagement with complementary projections on a positioning device. This arrangement provides a rigid, in particular rotationally stable connection between positioning device and locking nail. A rigid connection of this kind is very important for placement of the femoral-neck blade and the distal locking elements for the locking nail. It guarantees precise manipulation.

The long axis of the slanted passageway for the femoral-neck blade and the long axis of the proximal section of the locking nail enclose an angle of either 125° or 135°. These two embodiments of the passageway through the locking nail, which also define the position of the femoral-neck blade relative to the locking nail, have been found sufficient in practice. With these two angles all physiological variations of the angle between femoral neck and femoral shaft can be accommodated. A greater angulation away from the midline, by 140° or more, is not required with the system in accordance with the invention, which does not depend on force transmission through the bony cortex. Accordingly, when the osteosynthesis auxiliary in accordance with the invention is used, only two positioning bows are needed, one for 125° and another for 135°. Thus the number of instruments is minimized.

The average diameter of the locking nail in accordance with the invention is about 11–14 mm, preferably about 12 mm. This relatively slight diameter suffices because no transmission of force from the locking nail to the bone occurs or should occur. The force is imposed by way of the femoral-neck blade, through the intramedullary locking nail to the distal locking elements and thence to the distal femur. A large rigid locking nail, which would make direct contact with the femoral bone, would only be disadvantageous. There would be a danger that the nail would burst the femur, and a greater risk of fracture at the end of the nail.

Both in combination with the construction of an osteosynthesis auxiliary described above and independently thereof, i.e. for conventional constructions with femoral-neck screws, the femoral-neck part, i.e. either femoral-neck blade according to the present invention or conventional femoral-neck screw, comprises at its outer end, i.e. the end away from the head of the femur, a radially projecting section, in particular a circumferential collar, to limit the lateral extent to which the femoral-neck part can be introduced into the slanted passageway through the locking nail. Thus the femoral-neck part cannot accidentally be hammered too far into the slanted passageway through the locking nail, with the risk that under load the femoral-neck part will tip. into the varus position. It has been found in practice that after a femoral-neck part has become so tilted, it is extremely difficult to remove in the normal way. In the case of conventional femoral-neck screws, this danger is greatest when the selected femoral-neck screw is too short.

The femoral-neck part is constructed as a femoral-neck blade, wherein the section to be anchored in the head of the femur has a profile in the shape of a double-T or an I, a T, a star, a U or the like, preferably enclosing a central bore for a guide wire. These features can likewise be employed in combination with the construction previously described or independently thereof. This front end at the femoral neck part, which lies within the head of the femur, or the leading edges of the profiled section of the femoral-neck blade is or are constructed as cutting edges. The said design of the femoral-neck blade is distinguished by a high geometrical moment of inertia and hence by a correspondingly great resistance to bending combined with relatively thin-walled construction. Therefore only a small amount of spongiosa must be displaced when the femoral-neck blade is introduced or hammered into the neck and head of the femur. The introduction of the femoral-neck blade is a comparatively gentle procedure, in part because the leading edges are constructed as cutting edges.

The profile construction described above also ensures the above-mentioned rotational stabilization of the femoral head and/or neck with respect to the femoral-neck blade.

Moreover, if the femoral-neck blade with profile section were rotationally symmetrical in cross section, an additional means of securing it against rotation would have to be provided in the region of the slanted passageway through the locking nail. In this regard, reference is made to the state of the art as described above.

At least one transverse bore in the distal region of the locking nail is preferably elongated in cross section, forming an oblong transverse bore through which a distal locking element, in particular a distal locking bolt can be passed and anchored in the bone, such that the locking bolt for static distal locking of the locking nail is introduced at the proximal end and the locking bolt for dynamic locking of the locking nail is introduced at the distal end of the oblong transverse bore. These features can be employed independently of the construction described above. Accordingly, the length of the aperture of such an oblong transverse bore preferably corresponds to about twice the diameter of the associated locking bolt. In principle, a somewhat smaller or larger aperture length of the oblong transverse bore is also conceivable. This construction thus permits both a static distal locking of the locking nail and dynamic distal locking of the locking nail. In the known osteosynthesis auxiliaries of this kind, in contrast, only a static distal locking of the locking nail is possible, being accomplished by means of a bone screw passed through a distal transverse bore. In accordance with the invention this screw should also be replaced by a locking bolt having a self-cutting thread with only minimal thread depth, just sufficient to hold the locking bolt in the bone. The invention does not provide for pulling the locking bolt tight in the same way as a screw. On the contrary, in accordance with the invention such tightening should be avoided, because it has very often been found to produce weak points for a future fracture. The locking bolt in accordance with the invention should be held in the bone just firmly enough to prevent intramedullary slippage of the locking bolt with respect to the locking nail.

The distal locking bolt in accordance with the invention should be put in place by means of a positioning device, which for placement of the locking bolt in the oblong transverse bore comprises a positioning tube that can be turned by 180°, with a bore corresponding to the diameter of the locking bolt. A single such positioning device suffices for both the right and the left side of the patient. The positioning device is attached to the proximal end of the locking nail so as to form a rigid connection. This attachment is accomplished by either a screw or a catch mechanism. Furthermore, care should be taken that the positioning device operates without long lever arms, in order to prevent deformation due to grasping a lateral handle. In addition, the positioning device should be made in one piece in order to avoid relative movements between parts of the positioning device that could cause a deviation from predetermined targets (position of the femoral-neck blade on the one hand and position of the distal locking elements on the other hand). That is, the accuracy of positioning of the system must be ensured.

For the positioning of the distal locking elements, in particular locking bolts, the positioning device in accordance with the invention comprises, on an arm that in the assembled state extends approximately parallel to the locking nail in the direction toward its distal end, in association with at least one of the at least one oblong cross bore formed in the distal region of the locking nail, an elongated hole to receive a complementary positioning tube provided at its one end with a bore, the inside diameter of which is slightly greater than the outside diameter of a distal locking bolt to be passed through this bore. The positioning tube can be turned by 180° within said elongated hole, so that the one bore in the positioning tube can be brought into alignment with either the proximal or the distal end of the associated oblong cross bore in the distal region of the locking nail. After it has been placed in the said elongated hole of the is positioning device, the positioning tube is fixed in place by means of a fixation screw or the like.

So that the femoral-neck blade in accordance with the invention can be introduced, the positioning device is used to bore a hole in the corresponding region of the neck and head of the femur, by means of a graduated drill with a diameter of about 3.5 mm near the tip and about 10 mm elsewhere, the latter region serving to open up the space that will receive the lateral (distal) section of the femoral-neck blade. For the medial (proximal) profile section of the femoral-neck blade an initial bore with a diameter of about 3.5 mm suffices. The boring is accomplished by way of the positioning wire for the femoral-neck blade mentioned at the outset.

Regarding the above-mentioned oblong cross bores in the distal region of the locking nail it should be mentioned that a static distal locking is as a rule carried out in the case of normally oriented A1 and A2 peritrochanteric or femoral-neck fractures. A dynamic distal locking is used, e.g., for a transverse fracture of type A3 or a subtrochanteric fracture.

The above considerations, finally, make it evident that when the osteosynthesis auxiliary in accordance with the invention is used, a minimal number of instruments is required, namely:

Positioning device 125°;
Positioning device 135°;
Boring and centering sleeve for the femoral-neck blade;
Boring and positioning tube for the distal locking bolt;
Positioning wire for the femoral-neck blade (diameter about 3.0 mm), with associated hammering instrument for the femoral-neck blade, a screwdriver for the distal locking bolts and for the stay-pin associated with the femoral-neck blade (stud screw).

In the following an embodiment of an osteosynthesis auxiliary in accordance with the invention is explained with reference to-the attached drawings, wherein FIG. 1 shows a locking nail constructed in accordance with the invention, in lateral view;

FIG. 2 shows the locking nail according to FIG. 1 partially in longitudinal section, partially as viewed from the front;

FIG. 3 is an enlarged plan view of the proximal end of the locking nail in the direction of arrows A—A in FIG. 2;

FIG. 4 shows a femoral-neck blade constructed in accordance with the invention and associated with the locking nail as shown in FIGS. 1–3, in side view;

FIG. 5 shows the lateral (distal) end of the femoral-neck blade according to FIG. 4 in plan view;

FIG. 6 shows the medial (proximal) end of the femoral-neck blade according to FIG. 4 in enlarged plan view;

FIG. 7 shows enlarged the profile section of the femoral-neck blade according to FIG. 4 in section along the line A—A in FIG. 4.

Figure 8:
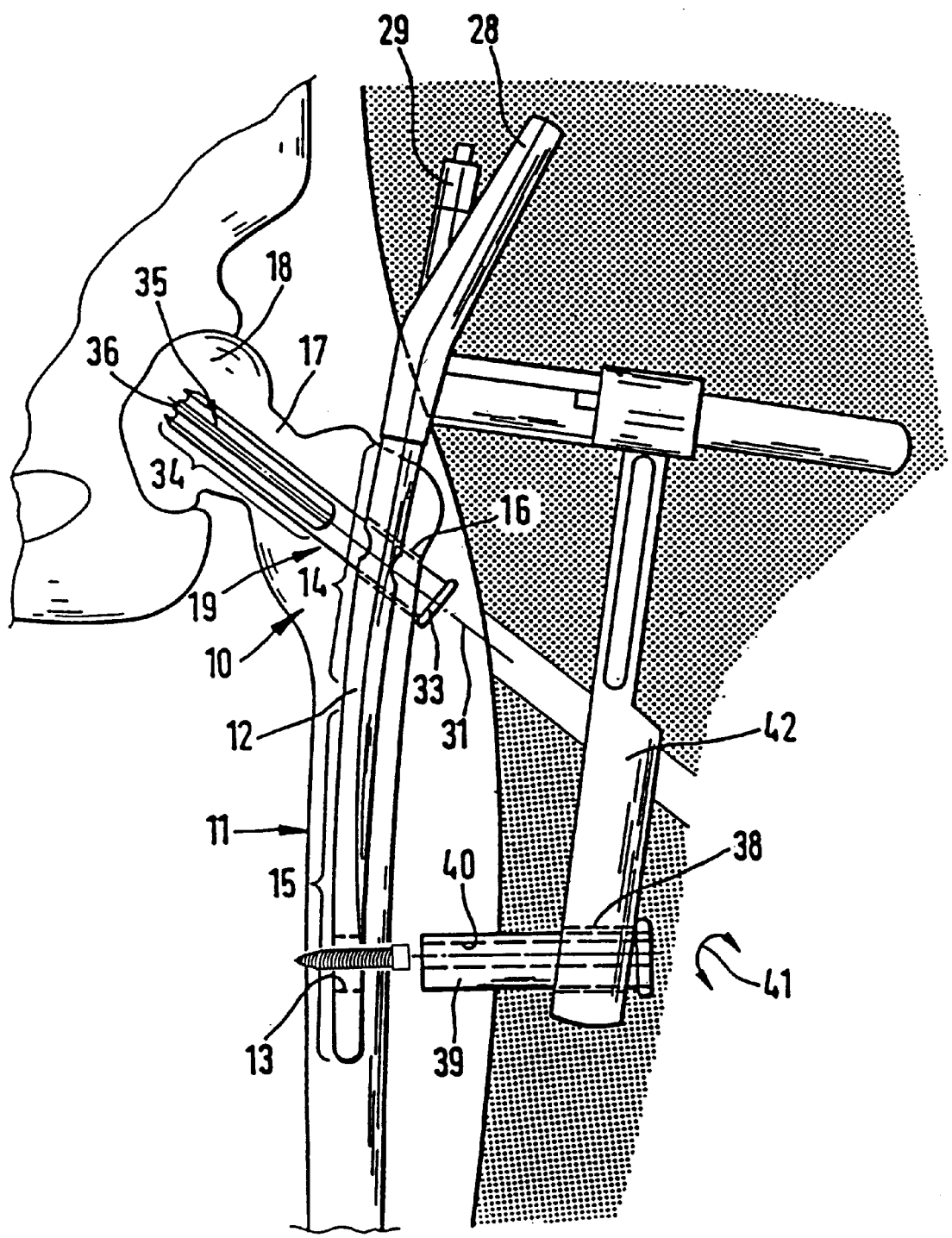
FIG. 8 shows the arrangement of locking nail, femoral-neck blade and associated positioning device relative to one another and to the femur, in schematic front view.

In FIGS. 1–8 an osteosynthesis auxiliary 10 (see FIG. 8) to treat subtrochanteric and peritrochanteric as well as femoral-neck fractures is shown, with a locking nail 12 that can be introduced from a proximal position into the medullary space of a femur 11, comprising a distal region with two oblong cross bores 13 to receive a distal locking element, namely a locking bolt 43, and a proximal section 14 with a slanted passageway 16, and with a femoral-neck part that can be introduced from a lateral position through the slanted passageway 16 into the neck 17 and head 18 of the femur, in the form of a femoral-neck blade 19 with basically rectangular cross section. The distal region of the locking nail 12 is identified by the reference numeral 15.

The cross section of the slanted passageway 16 corresponds to that of the femoral-neck blade 19, the femoral-neck blade 19 and passageway 16 being so dimensioned relative to one another that the femoral-neck blade 19 is held without play in the passageway 16. Into the proximal end 20 of the locking nail 12 can be introduced, namely screwed in, a stay-pin 44 (stud screw or the like). The corresponding threaded bore is identified in FIG. 2 by the reference numeral 21. By means of the stay-pin screwed into the threaded bore 21, axial movement of the femoral-neck blade 19 within the slanted passageway 16 can be either limited or completely prevented. For this purpose the section 22 (see FIG. 4) of the femoral-neck blade 19 associated with the passageway 16 comprises at least on the proximal (in the embodiment shown here, also on the distal) side a groove 23 parallel to the long axis, which engages the locking element that can be set into the proximal end 20 of the locking nail 21, or the above-mentioned stay-pin 44, as described. The one groove 23 can additionally comprise axially spaced-apart indentations 24 with which the stay-pin can interlock as needed, in order to produce a reliably rigid connection between locking nail 12 and femoral-neck blade 19. In this way, an axial movement of the femoral-neck blade 19 can be reliably prevented as required. Depending on the requirements, the femoral-neck blade 19 according to FIG. 4 can be provided on the side next to the stay-pin with either the axial groove 23 having the troughlike indentations 24 or the axial groove 23 that lacks said indentations. The former arrangement is selected in particular when the femoral-neck blade 19 is to be immobilized within the slanted passageway 16 of the locking nail 12. In this regard the embodiment according to FIG. 4 has a dual function.

As mentioned previously, the femoral-neck part in the embodiment described here has the form of a femoral-neck blade 19 with a cross section that is not circular or rotationally symmetrical but rather is rectangular. By this means, and by shaping the cross section of the slanted passageway 16 in the locking nail 12 correspondingly, rotation of the femoral-neck blade 19 within the slanted passageway 16 is permanently prevented. The rectangular passageway 16 is so oriented that the femoral-neck blade 19 is placed on edge therein, so that the flat sides of the femoral-neck blade 19 extend parallel to the long axis of the locking nail 12 or the neck of the femur. The described construction produces an especially large resistance to bending of the femoral-neck blade, with the consequence that there is no danger of the axial movement of the femoral-neck blade 19 being blocked by its becoming bent.

In the case of a dynamic placement of the femoral-neck blade 19 within the passageway 16, the dynamics are reliably preserved.

As can be seen in FIG. 2, the locking nail 12 is made hollow throughout its length (bore 25) so that it can be inserted into the proximal femur by a guide spike not shown here but known per se. The wall thickness of the hollow locking nail 12 is about 2.0 mm. The locking nail is made of a human-compatible material, in particular titanium or a titanium alloy. The same applies to the femoral-neck blade 19 and all other parts such as the stay-pin for the femoral-neck blade and the distal locking bolts.

As can further be seen in FIG. 2 and also FIG. 8, in the plane defined by locking nail 12 and femoral-neck blade 19 the proximal section 14 of the locking nail 12 is bent laterally outward with respect to its distal section 15, by about 6°, the transition between the distal and proximal sections being formed without an abrupt angulation, by a curved section 26.

The locking nail 12 in the embodiment shown here is rotationally symmetrical or circular in cross section. In principle an oval cross section is also conceivable, to enhance rotational stability of the osteosynthesis auxiliary within the femur.

Regarding the stay-pin for the femoral-neck blade 19, it should be mentioned that the stay-pin is recessed into the proximal end 20 of the locking nail 12 in a manner known per se.

To increase the stability of the locking nail 12 in the critical region of the passageway 16, this region is expanded relative to the distal region 15 of the locking nail 12. In concrete terms, the outside diameter of the locking nail 12 in the region of the passageway 16 is about twice as great as the diameter of the distal region 15. These dimensions ensure that even in the region of the passageway 16 the above-mentioned wall thickness of the locking nail 12 is retained. The danger of breakage of the locking nail 12 in the region of the passageway 16 is thereby eliminated.

In general, all transitions between the distal region 15 and expanded proximal region 14 should be constructed without sharp angles but with a gradual curvature, to prevent tension peaks in these transition regions.

As shown in FIGS. 1–3, in particular FIG. 3, at the proximal end 20 of the locking nail 12 three recesses 27 are uniformly distributed around its circumference to allow form-fitting engagement with complementary projections from a positioning device such as is indicated in FIG. 8 by the reference numeral 28. Owing to this positive engagement, which is additionally combined with a non-positive connection (stud 29 in FIG. 8 and associated threaded bore 30 in the proximal end 20 of the locking nail 12 as shown in FIG. 2), a rigid connection between positioning device 28 and locking nail 12 is obtained, which is necessary in order that the femoral-neck blade 19 and distal locking bolts can be accurately positioned.

The long axis 31 of the slanted passageway 16 for the femoral-neck blade 19 and the long axis 32 of the proximal section 14 of the locking nail 12 enclose an angle α of either 125° or, alternatively, 135°. The factors determining the choice between these alternatives are discussed above.

The femoral-neck blade 19, as shown in FIG. 8, comprises at its outer end, away from the head 18 of the femur, a radially projecting section in the form of a circumferential collar 33 that limits the lateral extent to which the femoral-neck blade 19 can be inserted into the slanted passageway 16 of the locking nail 12. This radial projection or collar 33 can also be usefully employed with conventional femoral-neck screws in order to avoid the dangers mentioned above with respect to driving in the femoral-neck blade or femoral-neck screw. Hence it is a separate structural characteristic of practical significance.

As shown in FIGS. 4, 6, 7 and 8, the section 34 of the femoral-neck blade 19 that can be anchored in the head 18 or neck 17 of the femur is constructed as a double-T or I profile 35 with a central bore 36 for a guide wire, not shown here but known per se. The leading end of the profile section 34, which lies within the head 18 of the femur, is constructed with chisel-like cutting edges 37, to make it easier to drive the femoral-neck blade 19 into the spongiosa of the neck and head of the femur without first opening up a space in the spongiosa as wide as the femoral-neck blade. As was mentioned above, by constructing the femoral-neck blade 19 with a double-T or I profile section 34 an extremely high geometrical moment of inertia is achieved, and hence an extremely high resistance to bending with minimal cross-sectional area, so that when the femoral-neck blade is driven into the neck and head of the femur, only a little spongiosa must be displaced. In addition, the profile section 34 promotes rotational stability of the head and neck of the femur in relation to the straight part of the bone when the auxiliary is used to treat femoral-neck or peritrochanteric fractures.

The two distal cross bores 13 in the distal region of the locking nail 12 are constructed as oblong cross bores, through which distal locking elements, namely locking bolts, can be passed to provide anchoring in the femoral bone, such that the locking bolts for static distal locking of the locking nail 12 are inserted at the proximal end (the upper end in FIGS. 1 and 2) and those for dynamic distal locking of the locking nail 12 are inserted at the distal end (the lower end in FIGS. 1 and 2) of the oblong cross bores 13. In the embodiment shown here, each of the oblong cross bores 13 has an aperture the length of which corresponds to approximately 2.5 times the diameter of the associated locking bolts or the width of the oblong cross bores 13.

The distal locking bolts are introduced by means of a positioning device 28. As explained above, the distal locking bolts should each comprise at the distal end a self-cutting thread with minimal thread depth. The thread should be just sufficient to hold the locking bolts in the femoral bone. In contrast to the state of the art, clamping by screw-tightening should not be allowed, in order to minimize the harm done to the bone.

With reference to FIG. 8, attention is again called to a positioning device suitable for use with the described osteosynthesis auxiliary, identified by the reference numeral 28. This can be attached at the proximal end 20 of the locking nail 12 in such a way as to form a rigid connection. It comprises an arm that in the assembled state extends approximately parallel to the locking nail 12 in the direction toward its distal end, and on this arm, in association with at least one of the at least one oblong cross bore 13 formed in the distal region of the locking nail 12, is disposed an elongated hole 38 to receive a complementary positioning tube 39, which is provided at its one end with a bore 40, the inside diameter of which is slightly greater than the outside diameter of a distal locking bolt to be passed through this bore. The positioning tube 39 can be turned by 180° in the elongated hole 38, so that the bore 40 in the positioning tube can be brought into alignment with either the proximal or the distal end of the associated oblong cross bore 13 in the distal region of the locking nail 12. That the positioning tube 39 can be turned by 180° in the manner described is indicated in FIG. 8 by the double-headed arrow 41. The bore 40 serves simultaneously as a sleeve for a drill with which openings are made in the femur to receive the distal locking bolts. On a line corresponding to an extension of the femoral-neck blade 19, the said arm 42 comprises an aperture to receive a boring and centering sleeve for the femoral-neck blade. These two sleeves are not shown in FIG. because they are known structural elements. The positioning device 28 is constructed in one piece in order to avoid shifting of its individual components with respect to one another. As a result, high positioning accuracy is achieved for the insertion of the femoral-neck blade as well as the distal locking bolts, after attachment to the locking nail 12.

When all the structural characteristics of the described system are combined in a single unit, an osteosynthesis auxiliary that is optimal in comparison to the state of the art is obtained, as the first trials by the inventor have already demonstrated.

All the characteristics disclosed in the application documents are claimed as essential to the invention, to the extent that they are new to the state of the art singly or in combination.

What is claimed is:

1. A method of treating femoral neck fractures which comprises:

placing a locking nail in the medullary space of a femur, said nail comprising a generally elongate body having a longitudinal axis and comprising a proximal portion and a distal portion, said axis being bent between said proximal and distal portions, said proximal portion having a transverse passageway inclined to said axis; driving a femoral neck blade through said passageway and into the neck of the femur;

said distal portion of said nail further comprising a cross bore having a generally oblong cross-section with a major axis of the oblong cross-section extending in the direction of the longitudinal axis of said nail, said method further comprising inserting a locking element through said cross bore and into the femur to anchor said nail to said femur and locating said locking element either at the proximal end of said bore for static connection of said nail to said femur or at the distal end of said bore for dynamic connection of said nail to said femur.

2. A method as claimed in claim 1, wherein the width of the oblong crossbore in the direction of said major axis is about twice the width of said locking element.

3. A method as claimed in claim 1, wherein said distal portion of said nail comprises two cross-bores; said method comprising inserting a second locking element into the second cross-bore and into the femur, said second locking element being located at the same end of the second bore as the first locking element is located in the first bore.

4. A method as claimed in claim 1, wherein said locking element comprises a self-tapping bolt.

* * * * *